(12) United States Patent
Buckley et al.

(10) Patent No.: US 9,744,143 B1
(45) Date of Patent: Aug. 29, 2017

(54) HONEY FORTIFIED WITH DIHYDROXYACETONE AND METHODS OF MAKING SAME

(71) Applicant: LINKS MEDICAL PRODUCTS INCORPORATED, Irvine, CA (US)

(72) Inventors: Thomas L. Buckley, Laguna Nigel, CA (US); Andrew Thain, Staffordshire (GB)

(73) Assignee: Links Medical Products, Inc., Irvine, CA (US)

( * ) Notice: Subject to any disclaimer, the term of this patent is extended or adjusted under 35 U.S.C. 154(b) by 0 days.

(21) Appl. No.: 15/369,978

(22) Filed: Dec. 6, 2016

(51) Int. Cl.
*A61K 35/64* (2015.01)
*A61K 31/121* (2006.01)
*A61K 35/644* (2015.01)

(52) U.S. Cl.
CPC .......... *A61K 31/121* (2013.01); *A61K 35/644* (2013.01)

(58) Field of Classification Search
None
See application file for complete search history.

(56) References Cited

U.S. PATENT DOCUMENTS

| | | | |
|---|---|---|---|
| 8,679,527 B2 | 3/2014 | Keiji et al. | |
| 9,446,079 B2 * | 9/2016 | Buckley | A61L 15/40 |
| 2011/0287059 A1 * | 11/2011 | Stephens | A23L 21/25 |
| | | | 424/278.1 |
| 2012/0021061 A1 * | 1/2012 | Schlothauer | A61K 45/06 |
| | | | 424/537 |
| 2015/0337019 A1 | 11/2015 | Johnson et al. | |
| 2016/0220722 A1 | 8/2016 | Wardell et al. | |
| 2016/0367606 A1 * | 12/2016 | Petito | A61K 35/644 |

* cited by examiner

*Primary Examiner* — Chris R Tate
*Assistant Examiner* — Randall Winston
(74) *Attorney, Agent, or Firm* — Jerry R. Potts; James R. McDaniel

(57) ABSTRACT

A dihydroxyacetone fortified honey composition, including a mixture of honey and dissolved dihydroxyacetone in a preferred honey to dissolved dihydroxyacetone ratio of 0.5 ml-20 ml of dissolved dihydroxyacetone to each kilogram of honey, wherein the mixture has a moisture content of between one and twenty percent, and wherein the mixture contains a preferred amount of methylglyoxal of between 83 milligrams of methylglyoxal per 1.0 kilogram of honey and 1500 milligrams of methylglyoxal per 1.0 kilogram of honey.

13 Claims, 1 Drawing Sheet

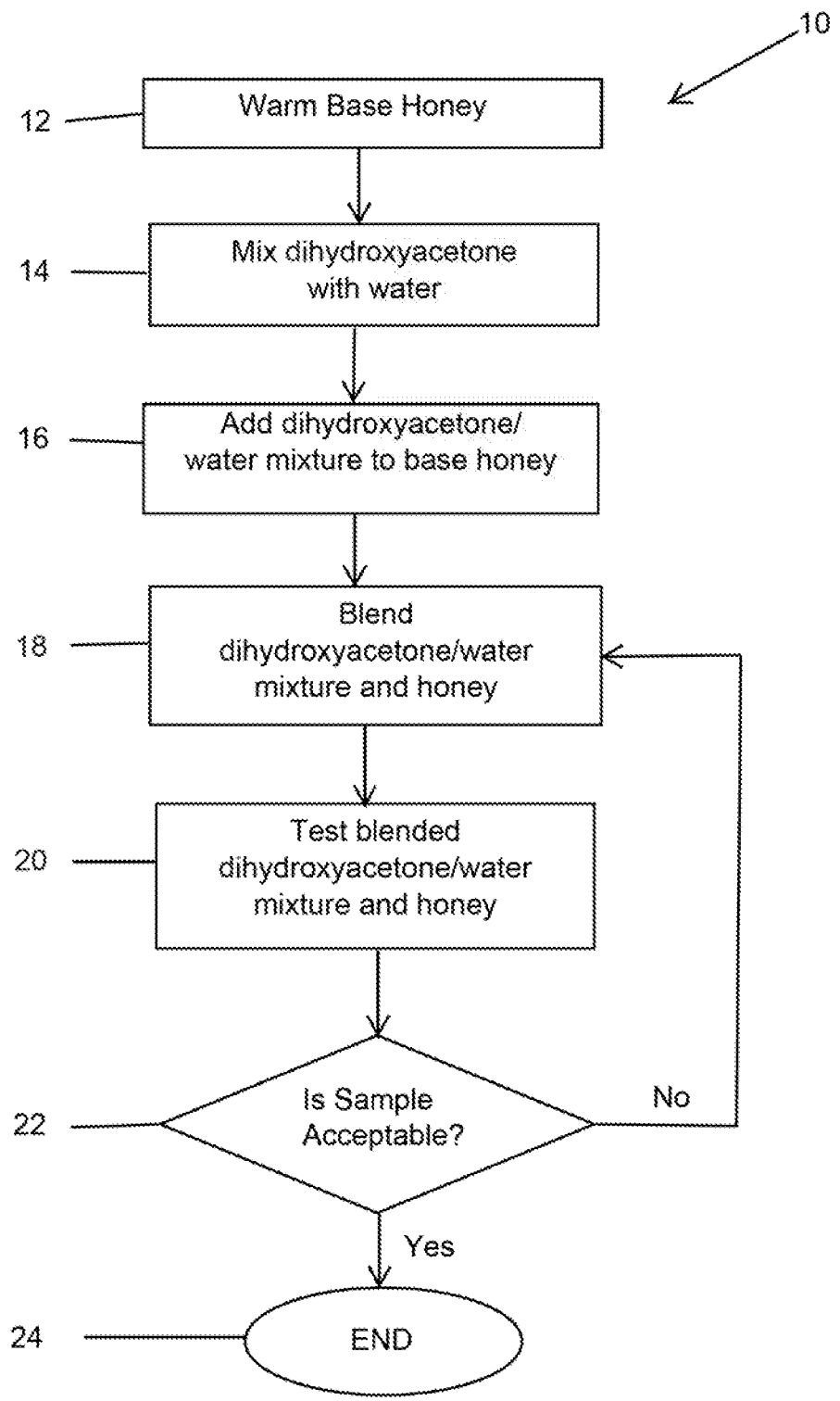

HONEY FORTIFIED WITH DIHYDROXYACETONE AND METHODS OF MAKING SAME

FIELD OF THE INVENTION

The present invention is generally related to honey that is fortified with dihydroxyacetone (DHA) in order to boost or enhance the production of methylglyoxal (MG) in the honey, and more particularly to a honey fortified with dihydroxyacetone and methods of making and using the dihydroxyacetone fortified honey.

BACKGROUND OF THE INVENTION

Prior to the present invention, as set forth in general terms above and more specifically below, it is known, to employ various antimicrobial compounds and compositions for the treatment or therapy for burns, ulcers and open wounds. See for example, U.S. Pat. No. 8,679,527 by Keiji et al., U.S. Patent Application Publication 2015/0337019 by Johnson et al. and U.S. Patent Application Publication 2016/0220722 by Wardell et al. While these various wound dressings, compounds and compositions may have been generally satisfactory, there is nevertheless a need for a new and improved honey that is fortified with dihydroxyacetone (DHA) in order to boost or enhance the production of methylglyoxal (MG) in the honey while guaranteeing antimicrobial activity level across the shelf life of the fortified honey.

It is a purpose of this invention to fulfill this and other needs in the medicine art in a manner more apparent to the skilled artisan once given the following disclosure.

BRIEF SUMMARY OF THE INVENTION

A first aspect of the present invention is a dihydroxyacetone fortified honey composition, comprising a mixture of honey and dissolved dihydroxyacetone in a preferred honey to dissolved dihydroxyacetone ratio of 0.5-20 ml of dissolved dihydroxyacetone to each kilogram of honey, wherein the mixture has a moisture content of between one and twenty percent; and wherein the mixture contains a preferred amount of methylglyoxal of between 83 milligrams of methylglyoxal per 1.0 kilogram of honey and 1500 milligrams of methylglyoxal per 1.0 kilogram of honey.

In one embodiment of the first aspect of the present invention, a more preferred honey and dissolved dihydroxyacetone is a ratio of 10 ml of dissolved dihydroxyacetone to each kilogram of honey; and a more preferred amount of methylglyoxal is at least 350 milligrams of methylglyoxal per 1.0 kilogram of honey.

In another embodiment of the first aspect of the present invention, the dissolved dihydroxyacetone is a mixture of dihydroxyacetone and a liquid at a preferred ratio of 20 g-60 g of dihydroxyacetone to every 100 ml of liquid.

In another embodiment of the first aspect of the present invention, the dissolved dihydroxyacetone is a mixture of dihydroxyacetone and a liquid at a more preferred ratio of 40 g of dihydroxyacetone to every 100 ml of liquid.

In another embodiment of the first aspect of the present invention, the liquid is further comprised of water.

In still another embodiment of the first aspect of the present invention, the honey is selected from the group consisting of any globally produced honey varieties including any globally produced honey varieties blended with corn syrup or sugar syrups.

In still yet another embodiment of the first aspect of the present invention, the dihydroxyacetone is further comprised of 50 to 99.9% pure dihydroxyacetone.

A second aspect of the present invention is a method of preparing a dihydroxyacetone fortified honey composition, comprising the steps of heating an amount of honey, wherein the honey contains less than 50 milligrams of methylglyoxal per 1.0 kilograms of honey and less than 200 milligrams of dihydroxyacetone per 1.0 kilograms of honey, mixing an amount of water with an amount of dihydroxyacetone to dissolve the amount of dihydroxyacetone in the water, blending the mixture of dissolved dihydroxyacetone and water with the amount of heated honey while maintaining a honey moisture content of between one and twenty percent, maintaining the blend of the mixture of dissolved dihydroxyacetone and water and heated honey at a desired temperature to allow the dihydroxyacetone to convert into methylglyoxal, and testing the blend of the mixture of dissolved dihydroxyacetone and water and heated honey to determine when a desired methylglyoxal level in the mixture of dissolved dihydroxyacetone and water and heated honey has been achieved.

In one embodiment of the second aspect of the present invention, maintaining a preferred ratio of honey and dissolved dihydroxyacetone of 0.5-20 ml of dissolved dihydroxyacetone to each kilogram of honey.

In another embodiment of the second aspect of the present invention, wherein a more preferred honey and dissolved dihydroxyacetone is a ratio of 10 ml of dissolved dihydroxyacetone to each kilogram of honey; and wherein the desired methylglyoxal level is between 350 and 1500 milligrams of methylglyoxal per 1.0 kilogram of honey.

In another embodiment of the second aspect of the present invention, wherein the step of heating includes heating the amount of honey to between 25 and 75° C.

In even further embodiment of the second aspect of the present invention, wherein the mixing step further includes dissolving the dihydroxyacetone with the water at a preferred ratio of 20 g-60 g of dihydroxyacetone to every 100 ml of water.

In still another embodiment of the second aspect of the present invention, wherein the mixing step further includes dissolving the dihydroxyacetone with the water at a more preferred ratio of 40 g of dihydroxyacetone to every 100 ml of water.

In yet another embodiment of the second aspect of the present invention, the honey is selected from the group including any globally produced honey varieties including any globally produced honey varieties blended with corn syrup or sugar syrups.

In an even further embodiment of the second aspect of the present invention, wherein the testing step further includes a more desired methylglyoxal level is at least 350 milligrams of methylglyoxal per 1.0 kilogram of honey.

A third aspect of the present invention is a method of preparing a honey composition, wherein the honey has been fortified with dihydroxyacetone in order to convert the dihydroxyacetone into methylglyoxal, comprising the steps of heating an amount of honey, wherein the honey contains less than 50 milligrams of methylglyoxal per 1.0 kilograms of honey and less than 200 milligrams of dihydroxyacetone per 1.0 kilograms of honey, mixing an amount of water with an amount of dihydroxyacetone to dissolve the amount of dihydroxyacetone in the water, blending the mixture of dissolved dihydroxyacetone and water with the amount of heated honey while maintaining a honey moisture content of between one and twenty percent, maintaining the blend of the mixture of dissolved dihydroxyacetone and water and heated honey at a desired temperature to allow a portion of the dihydroxyacetone to convert into methylglyoxal, and testing the blend of the mixture of dissolved dihydroxyacetone and water and heated honey to determine when a preferred methylglyoxal level of between 350 and 1500 milligrams of methylglyoxal per 1.0 kilogram of honey in the mixture of dissolved dihydroxyacetone and water and heated honey has been achieved In one embodiment of the third aspect of the present invention, wherein the step of blending includes maintaining a preferred ratio of honey and dissolved dihydroxyacetone of 0.5-20 ml of dissolved dihydroxyacetone to each kilogram of honey.

In another embodiment of the third aspect of the present invention, wherein the step of heating includes heating the amount of honey to between 25 and 75° C.

In still yet another embodiment of the third aspect of the present invention, wherein the mixing step further includes dissolving the dihydroxyacetone with the water at a preferred ratio of 40 g of dihydroxyacetone to every 100 ml of water.

In still another embodiment of the third aspect of the present invention, wherein the testing step further includes a more preferred methylglyoxal level is at least 350 milligrams of methylglyoxal per 1.0 kilogram of honey.

The preferred honey composition that is fortified with dihydroxyacetone (DHA), according to various embodiments of the present invention, offers the following advantages: ease of use of the composition for direct application to wounds and wound dressings; ease of use of the composition for use in cosmetics; ease of use of the composition for use in veterinary medicine; excellent light and heat stability of the composition; excellent anti-bacterial activity of the composition; excellent hygroscopic characteristics of the composition; the ability of the composition to provide nutrients to the wound bed; excellent anti-inflammatory characteristics of the composition; excellent pain relieving characteristics of the composition; reduced healing time of the wound; excellent debridement characteristics of the composition; increased antimicrobial characteristics of the composition; improved odor control by the composition; excellent osmotic absorption of excess exudate by the dressing during treatment; sustained and repeatable quality control; unlimited variety of honeys that can be fortified; and improved economic viability. In fact, in many of the preferred embodiments, these advantages are optimized to an extent that is considerably higher than heretofore achieved in prior, known honey-based compositions and dressings.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawing and in which:

FIG. 1 is a schematic illustration of the method of making a honey that is fortified with dihydroxyacetone (DHA) in order to boost or enhance the production of methylglyoxal (MG) in the honey, according to the present invention.

DETAILED DESCRIPTION OF THE PREFERRED EMBODIMENTS OF THE INVENTION

There is an urgent need for new, effective agents in topical wound care, cosmetics and veterinary care and selected honeys such as Manuka honey show potential in this regard. Manuka honey contains natural compounds including dihydroxyacetone (DHA) and methylglyoxal (MG). For clarity purposes, methylglyoxal is also sometimes called pyruvaldehyde or 2-oxopropanal, which is an organic compound expressed by the formula $CH_2C(O)CHO$.

Following research by the inventors, it has become apparent that DHA is responsible for the creation and maintenance of MG within the honey. It should be noted that MG is the antibacterial compound unique to Manuka honey.

However, due to the increased demand for Manuka honey, over the last five (5) years, the cost of Manuka honey has increased considerably, as shown in Table 1 below:

TABLE 1

|  | 2009/10 | 2010/11 | 2011/12 | 2012/13 | 2013/14 | 2014/15 |
| --- | --- | --- | --- | --- | --- | --- |
| Manuka NZ$ per kg | 7-37.5 | 8-80.50 | 8-50 | 10.45-60 | 8-85 | 9.5-116.5 |

As can be seen in Table 1, the global demand for Manuka honey has increased significantly over the last five (5) years with New Zealand now exporting an additional 2,000 tons of honey as compared to 2009/2010. As a direct result of potential supply disruption and rising honey costs, it is very desirable to be able to make a honey that is similar to Manuka honey in terms of its concentration of MG but at the same time avoids the high costs associated with the use of Manuka honey.

Referring now to FIG. 1, there is illustrated a method 10 for making a dihydroxyacetone (DHA) fortified honey that is similar to Manuka honey in terms of its concentration of MG but at the same time avoids the high costs associated with the use of Manuka honey. As will be explained hereinafter in greater detail, the dihydroxyacetone (DHA) fortified honey is prepared to provide antimicrobial, antibacterial and healing properties in the base honey, similar to those same properties as found in Manuka honey, by boosting or enhancing the production of methylglyoxal (MG) in the base honey. It is to be understood that in order for the resultant DHA fortified honey to exhibit the proper MG level, the MG level of the DHA fortified honey should contain a preferred amount of methylglyoxal of between 83 milligrams of methylglyoxal per 1.0 kilogram of honey and 1500 milligrams of methylglyoxal per 1.0 kilogram of honey with the preferred amount being between 350 mg/kg methylglyoxal and 1500 mg/kg methylglyoxal and the most preferred amount being at least 350 mg/kg methylglyoxal in order to be considered similar to medical grade honey.

With respect to the presently disclosed invention, the following should be considered relative to the honey component of the fortified honey. That is, honey is known to have a high osmolarity and solutions of high osmolarity are also known to cause the removal of water molecules from blood cells. In this regard, the outflow of lymph fluids created by the osmotic action of honey is beneficial to a healing process. This type of healing process is known as autolytic debridement. In short then, the outflow of liquid from a wound washes bacteria and dead wound cells to the surface and thus, into direct contact with the DHA fortified honey which promotes accelerated wound healing.

Preferably, the base honey to be fortified should contain from zero to a minimal amount (typically less than 50 mg/kg) of MG and only a limited amount of naturally occurring DHA (typically less than 200 mg/kg of DHA)

prior to fortification or "maturation". Honey fortified with DHA, according to the present invention, provides powerful antibacterial factors on infected wounds. Also, honey fortified with DHA, according to the present invention, has a number of properties that lend it for use in wound care dressings, cosmetics and veterinary medicine to name a few technologies. First, honey fortified with DHA has increased stability when exposed to light—and heat—such that honey fortified with DHA is not influenced by conventional sterilizing procedures. Second, honey fortified with DHA exhibits an osmotic absorption of excess exudate. Third, honey fortified with DHA exhibits an anti-bacterial activity that can inhibit the growth of bacteria and limit the production of the undesirable bi-products of bacterial growth. Fourth, honey fortified with DHA is hygroscopic which means it is capable of absorbing moisture from the air which, in turn, allows the fortified honey to be used effectively in moist wound care. Fifth, honey fortified with DHA provides beneficial nutrients to the wound bed. Sixth, the anti-inflammatory characteristics of honey fortified with DHA hasten the healing of wounds. Seventh, honey fortified with DHA can be used as a pain reliever due to the high sugar content in honey in that the fortified honey prevents pain during dressing changes because the fortified honey keeps the wound surface moist by mobilizing the edema from the surrounding tissues. Eighth, honey fortified with DHA can be used as a pain reliever by de-sensitizing the nerve endings due to inflammation. Ninth, the low pH level of honey fortified with DHA helps to reduce wound healing time by increasing the amount of oxygen off-loaded from hemoglobin in the capillaries in a wound area. Tenth, honey fortified with DHA provides an autolytic debridement characteristic by removing bacteria creating slough. Eleventh, honey fortified with DHA has high osmolarity (the concentration of an osmotically active substance in solution) which causes removal of water molecules from cells. Twelfth, honey fortified with DHA creates an enzymic production of hydrogen peroxide. Finally, honey fortified with DHA reduces the malodor from wound beds.

The honey component of the present invention is preferably any suitable honey selected from a group of honeys consisting of any globally produced honey varieties including any globally produced honey varieties blended with corn syrup or sugar syrups. Each of the above-mentioned honeys are all known to contain superior anti-bacterial and anti-inflammatory effects and thus, are preferred base honeys for the DHA fortified honey.

Regardless of which base honey is selected from the above-mentioned group for use in the honey fortified with DHA, it should be understood that one of the more important considerations is that ultimately, the minimum level of methylglyoxal in the resultant fortified honey preferably should be between 350 mg/kg methylglyoxal and 1500 mg/kg methylglyoxal with the more preferred amount being at least 350 mg/kg methylglyoxal in order for the resultant fortified honey to be recognized as similar to medical grade honey such as Manuka honey. This minimum level of MG is required in order to provide the minimum antimicrobial properties associated with medical grade honey such as Manuka honey.

Considering now the dihydroxyacetone (DHA) minimum level used during the manufacturing process to properly fortify the honey, the dihydroxyacetone (DHA) minimum level, preferably, is between 500 mg/kg of dihydroxyacetone (DHA) and 2000 mg/kg of dihydroxyacetone (DHA) with the more preferred amount being at least 750 mg/kg of dihydroxyacetone (DHA). This minimum level of dihydroxyacetone (DHA) is needed in order to provide the minimum amount of DHA that is needed to convert the DHA in the fortified honey into the required minimum amount of MG and to provide the proper shelf life for the fortified honey. It is to be understood that a three (3) year shelf life is typical for honey-based, wound care products. It is to be further understood that from studies conducted by the inventors, that the minimum level of 750 mg/kg of DHA is necessary to maintain the necessary 350+ mg/kg MG (or higher) across the three (3) year shelf life requirement of the resultant product. It is to be even further understood that any grade of DHA is suitable for fortifying the honey, however, the preferable grade of DHA is 50 to 99.99%+ pure DHA with the preferred purity being 99%. This particular grade of DHA is in line with international trade chemicals in that the 99% certified purity minimizes the potential for introduction of other impurities into the DHA fortified honey, while maximizing the level of DHA added.

Considering now the pH level of the honey fortified with DHA, preferably, the pH level of the resultant, fortified honey should be between 2 and 5. This pH range is desired since this is the natural pH range for all commercially traded honey. Also, this pH range is beneficial for treating wounds. It is to be understood that a wound pH level tends to be higher than 5, so the honey fortified with DHA would help to bring down the pH level in the wound which is conducive to wound healing.

Considering now the moisture level (or moisture content) of the honey fortified with DHA, preferably, the moisture level of the resultant, fortified honey should be less than 20 percent. This is a critical level since the resultant, fortified honey kept at a moisture level of less than 20 percent will substantially prevent fermentation and the growth of mold, mildew, fungus and yeast.

Considering now the natural sugar profile (the types of sugars in the honey and the concentrations of those sugars in the honey) in the honey fortified with DHA, the fortification of the honey with the DHA should not adversely change the sugar profile of the base honey. It is to be understood that the natural sugar profile of the honey is conducive to wound healing.

Method of Preparing the Dihydroxyacetone Fortified Honey

The following example is provided merely for illustrating the present invention and is not to be intended as limiting the scope of protection of the appended claims.

Example 1

1.) Composition
  A DHA fortified honey has been formulated with the following composition:
   a.) Batch size of honey could be between about one (1) KG and about 25,000 kg;
      i. Preferably, the batch size will be between about 1000 kg and 2000 kg of honey;
   b.) The methylglyoxal (MG) level of the resultant DHA fortified honey must be at least 350+ mg/kg MG; and
   c.) The dihydroxyacetone (DHA) minimum level added to the composition, preferably, is at least 750 mg/kg of dihydroxyacetone (DHA).
2.) Method (Step 10 of FIG. 1)
  The following steps were carried out:
   a.) Heat the base honey to between 25-70° C. (preferably between 35-45° C.) within a holding tank having built-in mixers/paddles (Step 12);
   b.) Mix between 20 g and 60 g, preferably 40 g of dihydroxyacetone (DHA), with 100 ml of liquid such as pure water until dissolved (Step 14). It is to be understood that the ratio of DHA to liquid must be such that the DHA addition is maximized and the water addition is minimized to the resultant product, without causing product manufacturing issues;

c.) Add between 0.5 and 20 ml, preferably 10 ml, of the DHA and pure water mixture to each kilogram of the heated honey (Step 16). Note that the ratio will change depending upon the amount of DHA that should be added to the base honey in order to achieve the desired amount of MG in the resultant product;

d.) Blend the DHA/pure water mixture with the heated base honey over a period of 1 week to 24 weeks with the more preferred time period being 3-6 weeks (Step 18). It is to be understood that this step is critical to ensure the desired homogeneity of each resultant product batch. It is to be further understood that the holding/mixing temperature must be controlled. As the honey and DHA/pure water mixture is warmed, the DHA starts to convert or "mature" into MG. The warmer the honey and DHA/pure water mixture, the faster the conversion. Extended blending times will allow one to reduce the temperature and still achieve the target MG levels. If the honey and DHA/pure water mixture is held at an ambient temperature, the conversion from DHA to MG is slowed. As the temperature reduces below ambient temperature, the DHA to MG conversion process slows considerably;

e.) Conventionally test the blended DHA/pure water and heated honey mixture to determine when the mixture has attained the desired MG levels, the desired DHA levels, the desired moisture levels and the desired sugar levels (Step 20). If the desired MG levels have not been attained, continue to blend the DHA/pure water and heated honey mixture (Step 22) until the desired MG levels, DHA levels, moisture levels and sugar levels are attained.

f.) Once the desired MG levels, DHA levels, moisture levels and sugar levels have been attained, pump the blended DHA/pure water and heated honey mixture into a holding container for shipping the bulk weight of the mixture to a converter (25 kg bucket, 280 kg drum, 1 ton IBC's and other storage options) (Step 24).

3.) Test Results

The following tests were carried out:

a.) Real-Time Storage Trial Tests
  i. The test objective is to understand the relationship between Dihydroxyacetone and Methylglyoxal and address the possibility of any synergistic effects. Samples to be kept at ambient (25° C.) and 37° C. temperatures.
  ii. The test demonstrates the interrelationship between DHA degradation and MG formation with time and impact of temperature effects.
  iii. The DHA transfer to MG is accelerated as the core temperature of the mix is increased.
  iv. Across all core temperatures, DHA transfer is at its fastest during the first 3 weeks of mixing process.
  v. Across all core temperatures, MG development is at its fastest during the first three weeks of the mixing process.

| 3 YEAR SHELF LIFE TESTING | | | | | |
|---|---|---|---|---|---|
| Honey Shelf (DHA/MG) Review | | AMBIENT 25 Degrees | | ACCELERATED 37 Degrees | |
| Day | Test Date | DHA | MGO | DHA | MGO |
| 1 | Jan. 31, 2014 | 4114 | 152 | 4114 | 152 |
| 13 | Feb. 13, 2014 | 3857 | 179 | 3378 | 420 |
| 21 | Feb. 21, 2014 | 3823 | 189 | 2822 | 641 |
| 31 | Mar. 3, 2014 | 3842 | 209 | 2929 | 624 |
| 96 | Jul. 5, 2014 | 3740 | 321 | 1387 | 786 |
| 137 | Jun. 17, 2014 | 3537 | 420 | 879 | 725 |
| 237 | Sep. 25, 2014 | 2954 | 593 | No reading taken | |
| 370 | Feb. 5, 2015 | 2362 | 679 | 171 | 280 |
| 728 | Jan. 29, 2016 | 1409 | 1073 | No reading taken | |
| 936 | Aug. 24, 2016 | 1164 | 994 | No reading taken | |
| | Jul. 31, 2017 | Reading to be taken January 2017 | | | | b.) Accelerated Production Tests
  i. The test objective is to take two 500 g blank runny honey samples with <50 MG/KG Methylglyoxal and add 2500 DHA to the first sample and 5000 DHA to the second sample. Both samples undergo "maturation" or conversion at 37° C. with MG/DHA testing at regular intervals after each test (first test at around 7-10 days). It is to be understood that it has been determined that 7-10 days is the most suitable first sampling point.
  ii. Necessary maturation/conversion time is estimated to be around 4-6 weeks. It is to be understood that maturation/conversion time will be determined by the product specification (the target MG levels). The higher the MG target level, the longer the maturation/conversion time.
  iii. Once the target MG level has been achieved, the samples will be submitted to 4-log Reduction tests, as shown below.

Results to Date:

| 37 Degrees - Standard Honey | | Standard Honey DHA 2500 | | Standard Honey DHA 5000 | |
|---|---|---|---|---|---|
| Days | Test Date | DNA | MG | DNA | MG |
| 0 | Jun. 21, 2016 | 0 | 0 | 0 | 0 |
| 1 | Jun. 22, 2016 | 2500 | 0 | 5000 | 0 |
| 10 | Jul. 1, 2016 | 2349 | 87 | 4599 | 174 |
| 24 | Jul. 15, 2016 | 2194 | 183 | 4264 | 388 |
| 34 | Jul. 25, 2016 | 2247 | 255 | 4414 | 532 |
| 41 | Aug. 1, 2016 | 2038 | 293 | 3984 | 540 |
| 50 | Aug. 10, 2016 | 1815 | 300 | 3614 | 572 |
| 64 | Aug. 24, 2016 | 1851 | 433 | 3730 | 783 |
| 71 | Sep. 1, 2016 | 1703 | 442 | 3317 | 878 |
| 80 | Sep. 9, 2016 | 1637 | 451 | 3189 | 853 |
| 86 | Sep. 15, 2016 | 1543 | 473 | 3085 | 911 |
| 115 | Oct. 14, 2016 | 1226 | 541 | 2461 | 999 |
| 148 | Nov. 16, 2016 | 1077 | 662 | 1973 | 1126 | c.) Accelerated Production Tests at 50° C. Heat
  i. The test objective is to take a blank sample of runny base honey with a <50 mg/kg Methylglyoxal reading. Add DHA to achieve target 5500 mg/kg DHA in product and heat at 50° C. in lab incubator.
  ii. Test Dihydroxyacetone and Methylglyoxal weekly.
  iii. Test at suitable time points as determined across the experiment, review growth acceleration/decline compared to 37° C. and ambient (25° C.) samples.
  iv. Within 7 days, medical grade honey (350+ mg/kg Methylglyoxal) can be manufactured.
  v. A maximum level of 884 mg/kg Methylglyoxal can be manufactured over the 62-week experiment.

vi. Re-fortification with Dihydroxyacetone during the manufacturing process does work, as demonstrated in stage2. An increased MG level of 1362 mg/kg Methylglyoxal was achieved 18 days after re-fortification with 5000 g/kg DHA, however this was only maintained for 1 week, before returning to 1000+ mg/kg Methylglyoxal levels.

Results to Date:

| T = Days | Date | DHA (mg/kg) | MGO (mg/kg) |
|---|---|---|---|
| | | 21929 - Stage 1-50 Degrees | |
| 0 | Aug. 24, 2016 | 5438 | 27 |
| 7 | Aug. 31, 2016 | 4089 | 457 |
| 16 | Sep. 9, 2016 | 3191 | 672 |
| 22 | Sep. 15, 2016 | 2770 | 765 |
| 29 | Sep. 22, 2016 | 2385 | 798 |
| 36 | Sep. 29, 2016 | 2166 | 777 |
| 44 | Oct. 7, 2016 | 1874 | 875 |
| 51 | Oct. 14, 2016 | 1523 | 871 |
| 62 | Oct. 25, 2016 | 1462 | 884 |
| | | 22579 - Stage 2 - Re-fortification - 50 Degrees | |
| 0 | Oct. 7, 2016 | 6912 | 850 |
| 7 | Oct. 14, 2016 | 4986 | 820 |
| 18 | Oct. 25, 2016 | 5016 | 1385 |
| 28 | Nov. 4, 2016 | 3915 | 1034 |
| 40 | Nov. 16, 2016 | 3007 | 1079 | d.) 4-Log Reduction Tests i. The 4-Log Reduction tests provide a quantitative measurement describing what percentage of the contaminants, which were present when the test began, was killed during the test and at what time.

ii. The test objective is to measure the performance of standard honey<50 mg/kg Methylglyoxal compared to Standard honey with 800+ mg/kg Methylglyoxal.

iii. The test demonstrates that the DHA fortified honey sample 800+ mg/kg Methylglyoxal outperformed the standard honey with <50 mg/kg Methylglyoxal. The DHA fortified honey reached the desired 4-log kill across all micros tested between 24 hrs and 5 days.

iv. The test also demonstrates that the base honey failed to reach the desired 4-log kill against any of the microorganisms tested. This clearly demonstrates the importance of the Methylglyoxal in fighting microorganisms.

language recited herein are principally intended expressly to be only for pedagogical purposes and to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents to the extent such incorporated materials and information are not inconsistent with the description herein.

| | PSEUDOMONAS AERUGINOSA | | STAPHYLOCOCCUS AUREUS | | CANDIDA ALBICANS | | STAPHYLOCOCCUS AUREUS (MRSA) | | ENTEROCOCCUS FAECALIS | |
|---|---|---|---|---|---|---|---|---|---|---|
| | Standard Honey | Standard Honey MG 800 | Standard Honey | Standard Honey MG 800 | Standard Honey | Standard Honey MG 800 | Standard Honey | Standard Honey MG 800 | Standard Honey | Standard Honey MG 860 |
| 0 HOURS | 0.04 | 0.02 | −0.3 | −0.02 | 0.004 | 0.02 | 0.03 | 0.06 | 0.02 | 0.02 |
| 4 HOURS | 0.09 | 0.07 | 0.04 | −0.02 | 0.02 | 0.06 | 0.05 | 0.08 | 0.03 | 0.02 |
| 24 HOURS | 0.94 | 3.03 | 0.24 | 0.26 | 0.04 | 4.48 | 0.33 | 0.32 | 0.09 | 0.04 |
| 5 DAYS | 3.39 | 5.03 | 2.2 | 4.74 | 0.97 | 5.48 | 0.61 | 5.18 | 1.1 | 4.33 |
| 7 DAYS | 3.46 | 5.03 | 3.37 | 5.74 | 1.34 | 5.48 | 1.59 | 6.18 | 1.49 | 5.33 |

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional The written description portion of this patent includes all claims. Furthermore, all claims, including all original claims as well as all claims from any and all priority documents, are hereby incorporated by reference in their entirety into the written description portion of the specification, and Applicant(s) reserve the right to physically incorporate into the written description or any other portion of the application, any and all such claims. Thus, for example, under no circumstances may the patent be interpreted as allegedly not providing a written description for a claim on the assertion that the precise wording of the claim is not set forth in haec verba in written description portion of the patent.

The claims will be interpreted according to law. However, and notwithstanding the alleged or perceived ease or difficulty of interpreting any claim or portion thereof, under no circumstances may any adjustment or amendment of a claim or any portion thereof during prosecution of the application or applications leading to this patent be interpreted as having forfeited any right to any and all equivalents thereof that do not form a part of the prior art.

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Thus, from the foregoing, it will be appreciated that, although specific embodiments of the invention have been described herein for the purpose of illustration, various modifications may be made without deviating from the spirit and scope of the invention. Other aspects, advantages, and modifications are within the scope of the following claims and the present invention is not limited except as by the appended claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention as defined by the appended claims.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

It is also to be understood that as used herein and in the appended claims, the singular forms "a," "an," and "the" include plural reference unless the context clearly dictates otherwise, the term "X and/or Y" means "X" or "Y" or both "X" and "Y", and the letter "s" following a noun designates both the plural and singular forms of that noun. In addition, where features or aspects of the invention are described in terms of Markush groups, it is intended and those skilled in the art will recognize, that the invention embraces and is also thereby described in terms of any individual member or subgroup of members of the Markush group.

Other embodiments are within the following claims. Therefore, the patent may not be interpreted to be limited to the specific examples or embodiments or methods specifically and/or expressly disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Other modifications and implementations will occur to those skilled in the art without departing from the spirit and the scope of the invention as claimed. Accordingly, the description hereinabove is not intended to limit the invention, except as indicated in the appended claims.

Therefore, provided herein are a new and improved honey composition that is fortified with dihydroxyacetone (DHA) and a novel method of preparing the honey composition that is fortified with dihydroxyacetone (DHA). The preferred honey composition that is fortified with dihydroxyacetone (DHA), according to various embodiments of the present invention, offers the following advantages: ease of use of the composition for direct application to wounds and wound dressings; ease of use of the composition for use in cosmetics; ease of use of the composition for use in veterinary medicine; excellent light and heat stability of the composition; excellent anti-bacterial activity of the composition; excellent hygroscopic characteristics of the composition; the ability of the composition to provide nutrients to the wound bed; excellent anti-inflammatory characteristics of the composition; excellent pain relieving characteristics of the composition; reduced healing time of the wound; excellent debridement characteristics of the composition; increased antimicrobial characteristics of the composition; improved odor control by the composition; excellent osmotic absorption of excess exudate by the dressing during treatment; sustained and repeatable quality control; unlimited variety of honeys that can be fortified; and improved economic viability. In fact, in many of the preferred embodiments, these factors of ease of use in treating wounds, cosmetics and veterinary medicine, ease of application of the composition to a wound dressing, excellent light and heat stability of the composition, excellent osmotic absorption of excess exudate by the dressing during treatment, excellent anti-microbial activity of the composition, excellent hygroscopic characteristics of the composition, the ability of the composition to provide nutrients to the wound bed, excellent anti-inflammatory characteristics of the composition, excellent pain relieving characteristics of the composition, reduced healing time of the wound, excellent debridement characteristics of the composition, increased antimicrobial characteristics of the composition, improved odor control of the composition, osmotic absorption of excess exudate by the dressing during treatment, sustained and repeatable quality, unlimited variety of honeys that can be fortified, and improved economic viability are optimized to an extent that is considerably higher than heretofore achieved in prior, known honey-based compositions and dressings.

We claim:

1. A method of preparing a dihydroxyacetone fortified honey composition, comprising the steps of:
    heating an amount of honey, wherein the honey contains less than 50 milligrams of methylglyoxal per 1.0 kilograms of honey and less than 200 milligrams of dihydroxyacetone per 1.0 kilograms of honey;
    mixing an amount of water with an amount of dihydroxyacetone to dissolve the amount of dihydroxyacetone in the water;
    blending the mixture of dissolved dihydroxyacetone and water with the amount of heated honey while maintaining a honey moisture content of between one and twenty percent;
    maintaining the blend of the mixture of dissolved dihydroxyacetone and water and heated honey at a desired temperature to allow the dihydroxyacetone to convert into methylglyoxal; and
    testing the blend of the mixture of dissolved dihydroxyacetone and water and heated honey to determine when a desired methylglyoxal level in the mixture of dissolved dihydroxyacetone and water and heated honey has been achieved.

2. The method of preparing a dihydroxyacetone fortified honey composition, according to claim 1, wherein the step of blending includes:
    maintaining a ratio of 0.5-20 ml of dissolved dihydroxyacetone to each kilogram of honey.

3. The method of preparing a dihydroxyacetone fortified honey composition, according to claim 2, wherein the honey and dissolved dihydroxyacetone is at a ratio of 10 ml of dissolved dihydroxyacetone to each kilogram of honey; and
    wherein the desired methylglyoxal level is between 350 and 1500 milligrams of methylglyoxal per 1.0 kilogram of honey.

4. The method of preparing a dihydroxyacetone fortified honey composition, according to claim 1, wherein the step of heating includes:
    heating the amount of honey to between 25 and 75° C.

5. The method of preparing a dihydroxyacetone fortified honey composition, according to claim 1, wherein the mixing step further includes:
    dissolving the dihydroxyacetone with the water at a ratio of 20 g-60 g of dihydroxyacetone to every 100 ml of liquid.

6. The method of preparing a dihydroxyacetone fortified honey composition, according to claim 1, wherein the mixing step further includes:
    dissolving the dihydroxyacetone with the water at a ratio of 40 g of dihydroxyacetone to every 100 ml of water.

7. The method of preparing a dihydroxyacetone fortified honey composition, according to claim 1, wherein the honey is selected from a group consisting of:
    any globally produced honey varieties including any globally produced honey varieties blended with corn syrup or sugar syrups.

8. The method of preparing a dihydroxyacetone fortified honey composition, according to claim 3, wherein the testing step further includes:
    the methylglyoxal level is at least 350 milligrams of methylglyoxal per 1.0 kilogram of honey.

9. A method of preparing a honey composition, wherein the honey has been fortified with dihydroxyacetone in order to convert the dihydroxyacetone into methylglyoxal, comprising the steps of:
    heating an amount of honey, wherein the honey contains less than 50 milligrams of methylglyoxal per 1.0 kilograms of honey and less than 200 milligrams of dihydroxyacetone per 1.0 kilograms of honey;
    mixing an amount of water with an amount of dihydroxyacetone to dissolve the amount of dihydroxyacetone in the water;
    blending the mixture of dissolved dihydroxyacetone and water with the amount of heated honey while maintaining a honey moisture content of between one and twenty percent;
    maintaining the blend of the mixture of dissolved dihydroxyacetone and water and heated honey at a desired temperature to allow a portion of the dihydroxyacetone to convert into methylglyoxal; and
    testing the blend of the mixture of dissolved dihydroxyacetone and water and heated honey to determine when a methylglyoxal level of between 350 and 1500 milligrams of methylglyoxal per 1.0 kilogram of honey in the mixture of dissolved dihydroxyacetone and water and heated honey has been achieved.

10. The method of preparing a honey composition for treating wounds, according to claim 9, wherein the step of blending includes:
    maintaining a ratio of honey and dissolved dihydroxyacetone of 0.5-20 ml of dissolved dihydroxyacetone to each kilogram of honey.

11. The method of preparing a honey composition for treating wounds, according to claim 9, wherein the step of heating includes:
    heating the amount of honey to between 25 and 75° C.

12. The method of preparing a honey composition for treating wounds, according to claim 9, wherein the mixing step further includes:
    dissolving the dihydroxyacetone with the water at a ratio of 40 g of dihydroxyacetone to every 100 ml of water.

13. The method of preparing a honey composition for treating wounds, according to claim 9, wherein the testing step further includes:
    a methylglyoxal level is at least 350 milligrams of methylglyoxal per 1.0 kilogram of honey.

* * * * *